United States Patent
Honigsbaum

(10) Patent No.: US 10,335,268 B2
(45) Date of Patent: Jul. 2, 2019

(54) ANTERIOR-POSTERIOR-CAPSULE-ACTUATED HYDRAULIC ACCOMMODATIVE INTRAOCULAR LENSES AND LENS SYSTEMS

(71) Applicant: Richard F. Honigsbaum, Passaic, NJ (US)

(72) Inventor: Richard F. Honigsbaum, Passaic, NJ (US)

( * ) Notice: Subject to any disclaimer, the term of this patent is extended or adjusted under 35 U.S.C. 154(b) by 0 days.

(21) Appl. No.: 15/966,829

(22) Filed: Apr. 30, 2018

(65) Prior Publication Data

US 2018/0243084 A1    Aug. 30, 2018

Related U.S. Application Data

(62) Division of application No. 15/175,707, filed on Jun. 7, 2016, now Pat. No. 10,182,905.

(60) Provisional application No. 62/173,771, filed on Jun. 10, 2015.

(51) Int. Cl.
*A61F 2/16* (2006.01)
*G02C 7/08* (2006.01)

(52) U.S. Cl.
CPC .......... *A61F 2/1629* (2013.01); *A61F 2/1627* (2013.01); *A61F 2/1648* (2013.01); *G02C 7/085* (2013.01); *A61F 2002/169* (2015.04); *A61F 2002/1682* (2015.04); *A61F 2230/0093* (2013.01); *A61F 2250/0003* (2013.01); *A61F 2250/0012* (2013.01); *A61F 2250/0053* (2013.01)

(58) Field of Classification Search
CPC .... A61F 2/1629; A61F 2/1627; A61F 2/1648; A61F 2/1624; A61F 2/1635; A61F 2/1651; A61F 2002/1682; A61F 2230/0093; A61F 2250/0003; A61F 2250/0012; A61F 2250/0053; G02C 7/085
See application file for complete search history.

(56) References Cited

U.S. PATENT DOCUMENTS

| | | | |
|---|---|---|---|
| 4,261,655 | A | 4/1981 | Honigsbaum |
| 7,261,737 | B2 | 8/2007 | Esch et al. |
| 7,985,253 | B2 | 7/2011 | Cumming |
| 2008/0300680 | A1* | 12/2008 | Joshua .................. A61F 2/1613 623/6.37 |
| 2009/0018652 | A1 | 1/2009 | Hermans et al. |
| 2011/0118834 | A1 | 5/2011 | Lo et al. |
| 2012/0303118 | A1 | 11/2012 | DeBoer et al. |
| 2016/0000558 | A1 | 1/2016 | Honigsbaum |

* cited by examiner

*Primary Examiner* — David H Willse
*Assistant Examiner* — Tiffany P Shipmon
(74) *Attorney, Agent, or Firm* — Cozen O'Connor

(57) ABSTRACT

An accommodative hydraulic intraocular lens system (AHIOL) has a cylindrical actuator contained within which is a hydraulic lens assembly. The hydraulic lens assembly has a transparent elastically reconfigurable membrane coupled to a fixed focus lens by a bellows and a refractive hydraulic fluid contained in the space defined by the membrane, the bellows and the lens, and is maintained at the upper range of its diopter power by the elastic properties of the bellows, springs, or both.

12 Claims, 2 Drawing Sheets

ANTERIOR-POSTERIOR-CAPSULE-ACTUATED HYDRAULIC ACCOMMODATIVE INTRAOCULAR LENSES AND LENS SYSTEMS

CROSS-REFERENCE TO RELATED APPLICATIONS

This application is a divisional U.S. patent application Ser. No. 15/175,707 which was filed with the U.S. Patent and Trademark Office on Jun. 7, 2016. Priority is claimed for this invention and U.S. Provisional Patent Application Ser. No. 62/173,771, filed on Jun. 10, 2015, which is incorporated by reference herein in its entirety.

BACKGROUND OF THE INVENTION

1. Field of the Invention

The present invention relates to hydraulic intraocular lenses and lens systems. Specifically, the present invention relates to hydraulic intraocular lenses and lens systems that address the compromising effects of capsulorhexis and the centripetal anterior forces that are lost thereby, that restore and maintain the spacing between the anterior and posterior capsule that is lost by crystalline lens extraction and that would otherwise result in the shrink-wrapping and fibrosing of the capsule and the loss of the accommodating function thereof, and that effect accommodation by employing the mechanisms that previously effected accommodation via the crystalline lens.

2. Description of the Related Art

When vision is compromised by cataracts, remediation typically comprises surgical extraction of the cataractous lens and the implantation of a single-focus intraocular lens. While this surgery would be an ideal opportunity to implant an intraocular lens that is also accommodative, none of the accommodative implants available to date provides the combination of the acuity of vision and the range of accommodation available from the combination of single focus implants and a pair of glasses having progressive lenses.

Hydraulic lenses, as described in the November, 1940 issue of the Journal of the Optical Society of America (JOSA), typically comprise a transparent plate to which is affixed a transparent elastically reconfigurable membrane, a refractive medium a portion of which is contained in the space between the membrane and the plate and the remainder of which is contained in an external reservoir, and a means for transferring refractive medium to and from the reservoir to the space, changing the curvature of the membrane and thus the diopter power of the lens thereby.

U.S. Pat. No. 4,261,655 to Honigsbaum, discloses a hydraulic lens in which the plate is an eyeglass lens, the external reservoir is a bellows, and the transfer means is a brow lever that flexes and relaxes the bellows, thus transferring refractive medium to and from the hydraulic lens and effecting change in diopter power thereby.

Published United States Patent Application 2011/0118834 to Lo et al discloses a hydraulic accommodative intraocular lens for implantation in the capsule of an eye from which the crystalline lens has been extracted, and in which the reservoir is in direct contact with the capsule equator.

U.S. Pat. No. 7,261,737 B2 to Esch et al and U.S. Pat. No. 7,985,253 B2 to Cumming disclose hydraulic lenses that are held in place in capsules by haptics that allow for space between the haptics and the capsulorhexis-compromised anterior capsule, and thus shrink-wrapping by, and fibrosing of, the capsule, and, as confirmed experimentally by Allo et al, Study of the force dynamics at the capsule interface related to ciliary body stimulation in a primated model, J Refrac Surg 2015 Feb. 31(2) pp 124-8, capsular forces intended to effect accommodation do not long survive shrink-wrapping.

Published U.S. Patent Application 2009/0018652 to Hermans et al discloses a two lens accommodative intraocular lens system that maintains separation between the anterior and posterior capsules and, because this prevents shrink-wrapping, continues to function accommodatively as confirmed by the continuing functionality of Synchrony Vu™ implants.

Hermans also discloses a plurality of actuating mechanisms for two-lens accommodative intraocular lenses, none of which anticipate either the hydraulic lens configurations or the actuating mechanisms of the present invention.

Published U.S. Patent Application 2016/0000558 (Honigsbaum) discloses tensioning rings for attachment to anterior capsules to restore at least a portion of the centripetal anterior capsular forces lost by capsulorhexis, spacer-actuators that prevent shrink-wrapping, and haptics-and-bellows actuated hydraulic accommodative intraocular lenses the bellows of which also serve as external reservoirs.

Published United States Patent Application 2012/0303118 (DeBoer et al) discloses a flexible bag for implantation in an eye from which the crystalline lens has been extracted, the bag to be filled with a compatible refractive medium after implantation, and some of the bag materials and refractive media are appropriate for the present invention as well.

Public domain lenses and lens systems are also described and illustrated herein for purposes of clarity of illustration and explanation.

SUMMARY OF THE INVENTION

The accommodative hydraulic intraocular lens system (AHIOL) of this invention comprises a cylindrical actuator contained within which is a hydraulic lens assembly.

The hydraulic lens assembly comprises a transparent elastically reconfigurable membrane coupled to a fixed focus lens by a bellows and a refractive hydraulic fluid contained in the space defined by the membrane, the bellows and the lens, and is maintained at the upper range of its diopter power by the elastic properties of the bellows, springs, or both.

The actuator comprises a pair of concentric cylinders one of which is coupled to the membrane and is in contact with one of the anterior and posterior capsule and the other of which is coupled to lens and is in contact with the other of the anterior and posterior capsule.

Thus, the lens system becomes disaccommodative when the anteriorly and posteriorly directed capsular forces previously applied to the crystalline lens to effect disaccommodation are applied to the cylinders, and accommodative when these forces are reduced to levels corresponding to accommodation of the crystalline lens. The actuator also maintains separation between the anterior and posterior capsules as did the crystalline lens.

The system also includes special features intended to address the compromising effects of capsulorhexis.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

The following description, given with respect to the attached drawings, may be better understood with reference to the non-limiting examples of the drawings, wherein.

DETAILED DESCRIPTION OF THE EXEMPLARY EMBODIMENTS

The description and the drawings to which the description refers are for purposes of explanation and illustration and are not for limiting the scope of the invention. The scope of the invention is defined by the claims.

Figure 1:
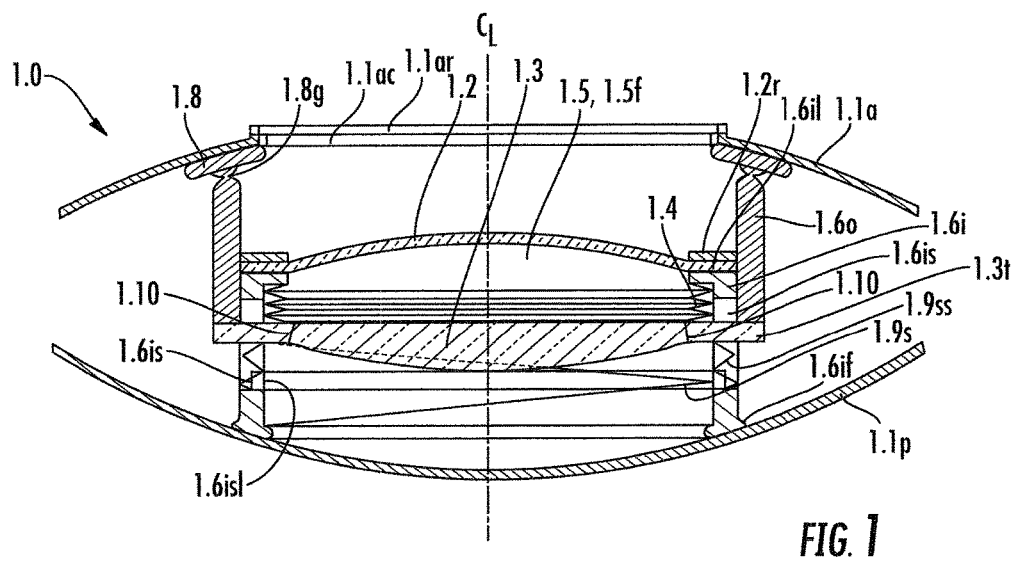
FIG. 1 is a sectional elevational view of an accommodative hydraulic intraocular lens (AHIOL) system in accordance with the present this invention implanted in the capsule an eye.

FIG. 1 is a sectional elevational view of the cutting plane for which includes and is defined by the centerline shown in the drawing, and shown therein is the relevant portion of the capsule of an eye from which the crystalline lens has been removed and into which an AHIOL system of this invention, generally designated as 1.0, has been implanted.

Parts of the eye, familiar from both the prior art and the literature, include anterior capsule 1.1a, posterior capsule 1.1p, and anterior capsulorhexis 1.1ac.

Hydraulic lenses typically comprise a transparent plate to which an elastically reconfigurable membrane is attached in such a way that the inner boundary of the attachment is a circle, a refractive hydraulic fluid part of which is contained in the space between the membrane and the plate and the remainder of which is contained in an external reservoir, and a means for effecting transfer of hydraulic fluid to or from the reservoir to the aforementioned space.

The hydraulic lens assembly of FIG. 1 comprises an elastically reconfigurable membrane 1.2, a fixed focus lens 1.3 which serves as the aforementioned plate, a tension bellows 1.4 (which, analogous to a tension spring, is at minimum axial length when unstressed, is elongated by forces parallel to its axis and directed away from one another, and returns to its unstressed length when these forces are removed) couples membrane 1.2 to fixed focus lens 1.3, and which is fixedly affixed directly or indirectly to both, a refractive hydraulic fluid chamber 1.5 defined by membrane 1.2, lens 1.3 and bellows 1.4 which serves as both the previously mentioned reservoir and the space between the membrane and the plate, and contained within which is refractive hydraulic fluid 1.5f. (While bellows 1.4 is shown as having a plurality of pleats for purposes of clarity of illustration, it is clear that the preferred number of pleats is a function of the elasticity of the bellows material, the refractive index of the hydraulic medium, the desired range of accommodation, etc., and that the number of pleats may, for these reasons, be greater or fewer than the three shown.)

The system further comprises a lens actuator comprising two concentric cylinders in slideable relationship, the inner of which 1.6i further comprises ledge 1.6il to the anterior face of which is fixedly affixed membrane 1.2 fixedly sandwiched between membrane ring 1.2r and ledge 1.6il, and to the posterior face of which is fixedly affixed the anterior end of bellows 1.4, the posterior end of which is fixedly affixed to fixed focus lens 1.3. The posterior end of inner cylinder 1.6i is intended for contact with posterior capsule 1.1p, and is shown as having a flexible flange 1.6if for the purpose.

Outer cylinder 1.6o is coupled to fixed focus lens 1.3 at its posterior face via lens tabs 1.3t which extend through slots 1.6is in inner lens actuator 1.6i, and is in contact with anterior capsule 1.1a at its anterior face. (Lens tabs 1.3t can be inserted into slots 1.6is by elastically deforming slots 1.6is and/or inner actuator 1.6i, or by making inner actuator 1.6i a two-part assembly fixedly affixed together at lap joint 1.6isl after lens tabs 1.3t are inserted into slots 1.6is.)

Thus, when the forces applied to outer cylinder 1.6o by anterior capsule 1.1a are increased by the increased zonular tension resulting from relaxation of the ciliary body muscle as explained in both the prior art and the literature, fixed focus lens 1.3 is translated posteriorly, expanding bellows 1.4, increasing the volume of chamber 1.5 containing refractive hydraulic fluid 1.5f, flattening membrane 1.2 and reducing the diopter power of the hydraulic lens as is appropriate for disaccommodation.

Conversely, when the ciliary body muscle contracts and zonular tension decreases, the posterior forces applied to outer cylinder 1.6o and thus fixed focus lens 1.3 also decrease, bellows 1.4 contracts (bellows contraction being assisted by optional compression springs 1.9ss in slots 1.6is, and/or spring 1.9s interposed between lens 1.3 and flange 1.6if if appropriate), and the curvature of membrane 1.2 and the diopter power of the hydraulic lens defined thereby increases as appropriate for accommodation.

AHIOL assembly 1.0, it should be noted, would also work as explained with respect to accommodation and disaccommodation if implanted inverted, i.e., with outer cylinder 1.6o in contact with posterior capsule 1.1p and inner cylinder 1.6i in contact with anterior capsule 1.1a, but the arrangement previously described is preferred because it moves the fixed focus lens posteriorly during disaccommodation and anteriorly during accommodation, thus aiding both. (It would, of course, be mandatory for alignment of the optical axis of the portion of the hydraulic lens between membrane 1.2 and fixed focus lens 1.3 with both the centerline shown in the drawing and the optical axis of the eye if fixed focus lens 1.3 includes prismatic correction.)

While posterior capsule 1.1p typically survives crystalline lens extraction and AHIOL implantation intact, anterior capsule 1.1a is compromised by capsulorhexis 1.1ac, and the loss of anterior capsule forces resulting therefrom, and this loss is addressed by prior art tensioning ring 1.1ar, by contact pads 1.8 (shown in section in FIG. 1 and in plan as 2.8 in FIG. 2) or by both.

(Tensioning rings are described in detail in the Honigsbaum application mentioned previously herein, and tensioning rings, as mentioned in that application, have penetrators that may be metal, and if so, and if springs 1.9s, 1.9ss etc., are also metal, these metals are preferably the same, or if not, at least biocompatible as the term is defined herein.)

Anterior capsule 1.1*a* also suffers a greater change in curvature from accommodation to disaccommodation than does posterior capsule 1.1*p* both in the presence of the crystalline lens as in the pre-presbyopic eye and after crystalline lens extraction and replacement with one of the AHIOLs of this invention, and contact pads 1.8 are pivotably connected to outer actuator 1.6*o* via bending grooves 1.8*g* to facilitate this.

Figure 4:
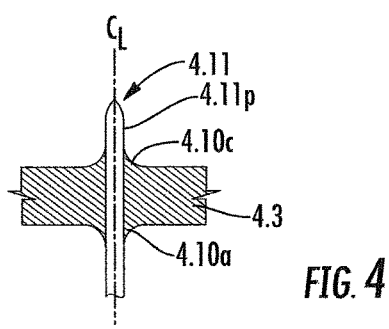
FIG. 4 is a fragmentary sectional view of the fill-and-purge ports and tips of FIG. 1.

FIG. 1 and its embodiments also include fill-purge ports 1.10 for filling hydraulic fluid chamber 1.5 with the required refractive hydraulic fluid 1.5*f* and purging it of bubbles before implantation, or it can alternately be filled and purged before implantation but implanted with some of the fluid withdrawn to facilitate folding, the remainder of the fluid being introduced via a fill-purge tip such as 4.11 of FIG. 4, the tubing connected thereto (not shown) left in place for the purpose and withdrawn after implantation.

Materials appropriate for the embodiments of FIG. 1 and the other accommodative intraocular lenses (AIOLs) of this invention include the silicone polymers employed in the manufacture of commercially available IOLs, and those and the other materials mentioned in DeBoer et al.

While the embodiments of FIG. 1 and the those of the other AHIOLs disclosed herein are intended to provide a range of accommodation greater than that available with a purely translational accommodative intraocular lens (AIOL), it is of interest to note that an embodiment of FIG. 1 from which membrane 1.2, bellows 1.4 and hydraulic fluid 1.5*f* were omitted, bellows 1.4 were replaced with a tension spring and/or optional spring(s) 1.9*s* and/or 1.9*ss* were included, would function as a purely translational AIOL, and, because it would also maintain separation between the anterior and posterior capsules, would not only be a viable alternative to haptic-actuated AIOLs that are rendered inoperative by shrink-wrapping of the capsule, but also be the fail-safe mode of FIG. 1 if the hydraulic lens portion thereof were to fail. Analogously, if membrane 1.2 were replaced with a negative (planoconcave or biconcave) fixed focus lens and bellows 1.4 etc. omitted, but its spring function retained as mentioned, it would further function as a purely translational two lens alternative to haptics-actuated two lens AIOLs that are also rendered inoperative by shrink-wrapping.

It is also of interest to note that none of the AHIOL embodiments shown in the drawings have haptics, but then neither do the crystalline lenses they are intended to replace, and both for the same reason: both kinds of lenses are centered by the elastic fibers of their respective capsules, provided, of course, that, with respect to the embodiments of this invention, the capsulorhexi and the tensioning rings (if present) are well centered.

There is, however, the matter of the fixed focus lenses of this invention that require a predetermined fixed orientation with respect to a nasal-temporal line, e.g., lenses that include prismatic correction and toric lenses that include correction for astigmatism, and the forces that serve to maintain this orientation are provided by the interaction of spaces between pads 1.8 of FIG. 1 (shown as spaces 2.8*s* in FIG. 2) with the elastic fibers of the adjacent capsule.

Figure 2:
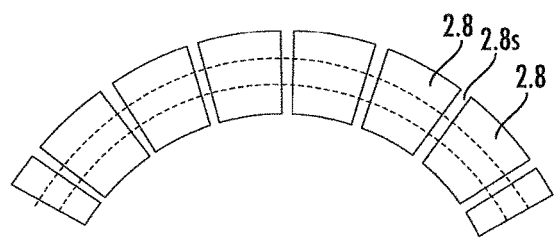
FIG. 2 is a fragmentary anterior plan view of the AHIOL of FIG. 1.

FIG. 2 is a fragmentary plan view of the anterior face of the lens system of FIG. 1, and as is clear from the drawing, there is a space 2.8*s* between each pair of pads 2.8, this to eliminate the possibility of the pads interfering with one another during the above-mentioned change in curvature, and for other reasons mentioned previously herein.

Figure 3:
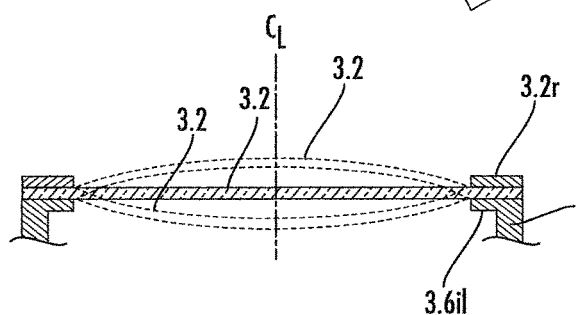
FIG. 3 is a fragmentary sectional elevational view of the membrane portion of FIG. 1.

FIG. 3 is a fragmentary sectional elevational view of the anterior portion of the inner actuator 1.6*i* of FIG. 1 that illustrates extremes in membrane 1.2 (3.2*a*, *b* & *c* in FIG. 3) configuration during actuation of the accommodative-disaccommodative mechanism of FIG. 1. Also shown in FIG. 3 is a fragment of inner actuator 1.6*i* and its ledge 1.6*il* (here labeled 3.6*i* and 3.6*il* respectively). Also shown, but not previously described, is membrane ring 1.2*r*, here labeled 3.2*r*.

While membrane 3.2 is fixedly affixed to ledge 3.6*il*, flexing through the range shown in the drawing alternately loads the bond between the membrane and the ledge in compression and peel, the kind of cycling most likely to destroy the bond between the two, and the risk mentioned is addressed herein by fixedly sandwiching membrane 3.2 between ledge 3.6*il* and membrane ring 3.2*r* (1.2, 1.6*il* and 1.2*r* in FIG. 1 respectively).

Membrane 3.2 also suffers a change in tension as it is cycled over the range shown in FIG. 3 and is most likely to wrinkle in the middle position, and this risk of wrinkling is addressed by pre-loading the membrane in tension, fixedly affixing ring 3.2*r* to the pre-loaded membrane (or vice versa), trimming off excess membrane as appropriate, and then fixedly affixing the membrane-ring combination to ledge 3.6*il* and thus to inner actuator 3.6*i* (1.6*i* in FIG. 1).

While it seems obvious that the above could be addressed by simply choosing a refractive hydraulic medium that allows limiting the excursion of the membrane to the convex shape shown in FIG. 1, it is important to note that the lens defined by the membrane and the refractive medium is not a simple convex spherical lens, but one complicated by the fact that the membrane is constrained at its periphery, and that while aberrations resulting from this and its idealization as a simple planoconvex lens can be corrected for one radius of membrane curvature by making fixed focus lens 1.3 appropriately aspheric, other membrane curvatures are not.

Thus the preferred arrangement is one in which most of the diopter power needed to replace that lost by crystalline lens extraction is provided by the fixed focus lens, the AHIOL is oriented as shown in FIG. 1 to take advantage of the accommodating and disaccommodating effects of the anterior-posterior translation of the fixed focus lens, and the accommodative range provided by the membrane is limited to that needed to perform a normal range of visual tasks which, based upon the "add" portion of eyeglasses prescribed for presbyopic patients, is typically less than about four diopters.

Membrane 3.2 (1.2 in FIG. 1) is shown and described as being fixedly affixed to another component of the embodiment, as are other components thereof, and this bonding can, for most components, be effected by gluing, solvent gluing, thermal fusion, the curing together of tacky components, etc., affixing of the membrane requires special consideration because injudicious choice of method can compromise the mechanical and/or optical properties of the membrane, and the presently preferred method is, for this reason, a low temperature thermosetting glue.

FIG. 4 is a fragmentary sectional view of the fill-purge ports 1.10 of the embodiments of FIG. 1 and those of the other AHIOL embodiments of this invention, the purpose of which is to facilitate the filling of chambers such as 1.5 with refractive hydraulic fluid and the purging of bubbles therefrom, and the ports are on opposite sides of their respective chambers to facilitate this.

Because membranes 1.2, 3.2, etc., can cycle from convex to plano to concave and vice versa, the pressures in the corresponding hydraulic fluid chambers can cycle through ranges that may be higher or lower than local ambient, and the ports have for this reason a pair of mechanically penetrable seals 4.10a, c, each much like those familiar from spray cans, one at each end, to block flow into or out of the hydraulic chambers once tubular fill-purge tips 4.11 are withdrawn. (If, however, the pressure difference between chambers such as 1.5 and the lens system ambient does not change sign, the seal corresponding to 4.10 a or c on the low pressure side can be omitted.)

Figure 4A:
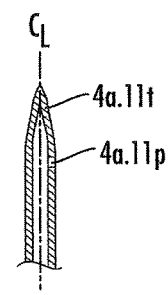
FIG. 4a is a detailed sectional view of the end portion of the fill-purge tips of FIG. 4.

Tips 4.11, the end portions of which are shown in greater detail in FIG. 4a, also preferably have tapered, blunt-pointed ends 4a.11t and side openings 4a.11p, rather than the more familiar sharp ends and end openings which can damage seals such as 4.10a, c during tip insertion.

Figure 5:
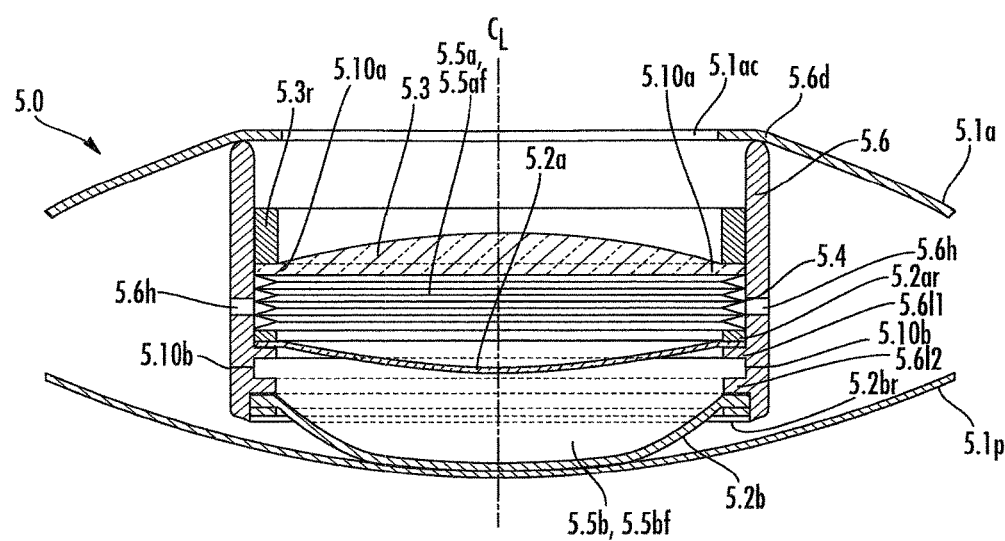
FIG. 5 is a sectional elevational view of a two-chambered AHIOL in accordance with the present invention.

FIG. 5 is a sectional elevational view of an alternate embodiment of this invention, generally designated 5.0 in the drawing, the cutting plane for which is again defined by the centerline shown in the drawing, and is a two-hydraulic-chamber AHIOL, one chamber of which, 5.5a, is defined by the now familiar fixed focus lens 5.3, membrane 5.2a fixedly affixed to ledge 5.6/1 of support structure 5.6 (analogous to inner actuator 1.6i of FIG. 1) or sandwiched between ledge 5.6/1 of support structure 5.6 and membrane ring 5.2ar, and tension bellows 5.4, one end of which is fixedly affixed to lens 5.3 and the other to ring 5.2ar (or directly to membrane 5.2a if ring 5.2ar is omitted). The other chamber, 5.5b, is defined by membrane 5.2a, membrane 5.2b preferably fixedly sandwiched between second ledge 5.6/2 and second membrane ring 5.2br or, if ring 5.2br is omitted, fixedly affixed to ledge 5.6/2, and the portion of support structure 5.6 between membranes 5.2a and 5.2b.

Chamber 5.5a is filled with refractive hydraulic fluid 5.5af which, like refractive hydraulic fluid 1.5af of FIG. 1, has an index of refraction different from that of aqueous humor, and, like fluid 1.5af, is the refractive medium of a lens the curvature and hence the diopter power of which is determined by the curvature of elastically reconfigurable membranes 1.2 and 5.2a of FIGS. 1 and 5 respectively, while chamber 5.5b is filled with hydraulic fluid 5.5bf having a refractive index substantially equal to that of aqueous humor, and except as it changes the curvature of membrane 5.2a as explained below, has no effect with respect to the diopter power of the AHIOL of FIG. 5.

Each chamber also has a pair of fill-purge ports, 5.10a for chamber 5.5a, and 5.10b for chamber 5.5b respectively.

Thus, when increased posterior forces are applied to support structure 5.6 by anterior capsule 5.1a and increased anterior forces are applied to membrane 5.2b by posterior capsule 5.1p, membrane 5.2b is flattened and some of fluid 5.5bf is transported anteriorly, flattening membrane 5.2a which in turn moves lens 5.3 (which has a sliding fit with respect to support structure 5.6) anteriorly, and the AHIOL of FIG. 5 becomes disaccommodative. Conversely, when these forces are decreased, membrane 5.2b becomes more convex as does membrane 5.2a, and the AHIOL becomes accommodative.

This change in accommodation, and thus the diopter power of the AHIOL, is further facilitated by the tensional springiness inherent in tension bellows 5.4, a tensional spring introduced for the purpose (not shown), or both.

Also shown in FIG. 5 is anti-tilt ring 5.3r, one of integral with and fixedly affixed to lens 5.3, and which also has a sliding fit with respect to, support structure 5.6. The purpose of anti-tilt ring 5.3r is to maintain collinearity of the optical axis of lens 5.3 with the centerline shown in the drawing, and thus with the optical axis of lens membrane 5.2a.

While FIG. 1 embodiments can be implanted either oriented as shown in the drawing or inverted, those of FIG. 5 as shown in the drawing cannot, because doing so would cause membrane 5.2b to protrude through anterior capsulorhexis 5.1ac, make contact with the iris, and compromise the aqueous humor drainage path. It can, however, be implanted inverted if the anterior capsule contact portion of membrane 5.2b that bridges capsulorhexis 5.1ac is made stiff enough, say by thickening, to bridge the capsulorhexis without the protruding mentioned, and by widening support structure 5.6 as necessary to accommodate the flexing of the portion of membrane 5.2b between its thicker portion and support structure 5.6. It would also be appropriate to affix a tensioning ring such as 1.1ar of FIG. 1 to anterior capsule 5.1a not only for the purpose for which it is intended, but also to prevent stretching and/or tearing of the capsulorhexis by membrane 5.2b.

FIG. 5 embodiments also preferably include holes 5.6h shown in support structure 5.6 of FIG. 5, the purpose of which is to eliminate the possibility that aqueous humor entrapped between bellows 5.4 and support structure 5.6 will interfere with the above-mentioned change of curvature of membrane 5.2a, and thus the change in diopter power of the AHIOL. Such entrapment and the aforementioned consequences thereof can also alternately or additionally be eliminated by the introduction of axis-parallel grooves (not shown) in the corresponding parts of the surfaces of lens 5.3 and ring 5.3r in contact with support structure 5.6.

Because the embodiment of FIG. 5 when implanted as shown in the drawing also increases the risk of entrapping cells left over from capsulorhexis and/or crystalline lens extraction between membrane 5.2b and posterior capsule 5.1p, and thus the risk of posterior capsular obscuration, but because coating and/or impregnating membrane 5.2b with a cell growth inhibitor such as fu5 could also adversely affect the posterior capsule if implanted as shown in the drawing, FIG. 5 embodiments are preferably implanted inverted so that not only are optical surfaces in contact with the aqueous humor but isolated from direct contact with capsules by parts of actuators such as the convex faces of lenses 5.3, but also center parts of membranes 5b, which are isolated from direct contact with the anterior capsule by capsulorhexii when FIG. 5 embodiments are implanted inverted, can be so treated. (Such remediation can, of course, also be applied to both lens 1.3 and membrane 1.2 of FIG. 1, both of which are isolated from direct contact with the capsule by cylinders 1.6i and 1.6o, and to the parts of cylinders 1.6i and 1.6o in sliding contact with one another.)

FIG. 5 embodiments can, as mentioned, be implanted in a capsule oriented as shown in the drawing or inverted, and the treatment of the end of support structure 5.6 distal from membrane 5.2b is preferably determined in accordance with FIG. 1. Thus, if distal end 5.6d, which is shown in the drawing as a simple rounded edge, is to be in contact with an anterior capsule it would preferably be configured as is the anterior capsule-proximal end of outer cylinder 1.6o of FIG. 1, while if distal end 5.6d is to be in contact with the posterior capsule end it would be preferably configured as is the posterior capsule proximal end of inner cylinder 1.6i.

Definitions

The term "translation" is used herein as in classical mechanics to describe motion in a straight line. Ophthalmologists use the term "vaulting" to describe such motion with respect to AIOLs.

The term "biocompatible" is used herein to describe the man-made materials used in the practice of the present invention that are compatible with an eye and its components both alone in an eye and in the presence of other such materials.

The term tension bellows" is used herein to refer to a cylindrical bellows the axial length of which is minimum when the bellows is unstressed, and that, if external forces applied to it to increase its length are removed, will return to its unstressed length.

The term "fixedly sandwiched" as used herein refers to a component of this invention at least a portion of which is fixedly affixed to two other components, one on each side.

Thus the new, novel and useful features of the present invention have been disclosed in the drawings and descriptions herein. These drawings and their descriptions are intended to be illustrative rather than limiting, the invention being defined by the claims appended hereto.

What is claimed is:

1. A biocompatible accommodative hydraulic intraocular lens (AHIOL) system for implantation in the capsule of an eye from which the crystalline lens has been extracted via anterior capsule capsulorhexis, the system comprising:
 a self-reservoired hydraulic lens and an actuator for the hydraulic lens;
 the actuator comprising a coaxial pair of cylinders having an outer cylinder and an inner cylinder in sliding relationship with one another, the outer cylinder comprising an inner ledge and an end configured for contact with one of an anterior and a posterior capsule, the inner cylinder comprising a plurality of substantially axis-parallel slots at one end and an end configured for contact with the other of the anterior and posterior capsule;
 the hydraulic lens comprising a fixed focus lens in slideable relationship with respect to an inner actuator and further comprising a plurality of radial tabs at the inner cylinder slots and extending therethrough, an elastically reconfigurable transparent membrane one of fixedly affixed to the ledge and fixedly sandwiched between the ledge and a membrane ring, and a tensional bellows, one end of which is fixedly affixed to the fixed focus lens and the other end to the ledge,
 wherein a closed hydraulic fluid chamber is defined by the transparent membrane, the tensional bellows, the fixed focus lens and the ledge, the fluid chamber containing a refractive hydraulic fluid having an index of refraction greater than that of aqueous humor.

2. The system of claim 1, wherein the capsulorhexis is substantially axisymmetric.

3. The system of claim 1, further comprising an anterior capsule tensioning ring.

4. The system of claim 1, further comprising at least one compression spring contained within a portion of one of the substantially axis-parallel slots located between a corresponding radial tab of the fixed focus lens and a ledge-distal end of one of the substantially axis-parallel slots.

5. The system of claim 1, wherein each cylinder has a capsule-contacting end intended for contact with the anterior capsule, wherein each cylinder further comprises a flexible flange, and a plurality of pivotably attached pads at the end of each cylinder.

6. The system of claim 1, wherein the closed hydraulic fluid chamber further comprises at least one fill-purge port.

7. The system of claim 1, wherein the lens comprises one refractive face and one plano face, and wherein the plano face is in contact with the refractive hydraulic fluid.

8. The system of claim 1, wherein the fixed focus lens comprises correction for the aberrations of the fixed focus lens, the transparent membrane and the eye, and also for most of the diopter power of the eye lost by crystalline lens extraction.

9. A biocompatible accommodative translational intraocular lens (ATIOL) system for implantation in the capsule of an eye from which the crystalline lens has been extracted via a capsulorhexis, the system comprising:
 an actuator, at least one fixed focus lens and at least one spring;
 the actuator comprising a pair of concentric cylinders having an outer cylinder and an inner cylinder in slideable relationship therewith, the inner cylinder comprises a plurality of axis-parallel slots, a ledge at one end and an end modified for contact with the capsule at the other, the axis-parallel slots containing the first fixed focus lens, the first fixed focus lens further comprising a same plurality of tabs, each tab extending through a corresponding slot and in slideable relationship with the inner cylinder;
 the outer cylinder comprising one end modified for contact with the capsule and the other for contact with the fixed focus lens tabs; and
 the at least one spring comprising at least one of a compression spring interposed between the ledge and the fixed focus lens and at least one compression spring contained in the part of a slot between the lens tabs and the ledge-distal slot part of the slot.

10. The system of claim 9, wherein the cylinder ends are configured for contact with the capsule, and wherein each cylinder further comprises a flexible flange, and a plurality of pivotably attached pads at the end of each cylinder.

11. The system of claim 9, further comprising a second lens fixedly affixed to the ledge.

12. The system of claim 11, wherein the lens intended for proximity to the anterior capsule further comprises a lens that is one of plano-convex and biconvex, and wherein the lens intended for proximity to a posterior capsule further comprises a lens that is one of plano-concave and bi-concave with one of its faces being convex for correction for aberration of itself and the eye, and for most of the diopter power of the eye lost by crystalline lens extraction.

* * * * *